United States Patent [19]

Bouser

[11] Patent Number: 5,520,671

[45] Date of Patent: May 28, 1996

[54] URINAL DEVICE

[76] Inventor: Richard E. Bouser, P.O. Box 464, Brookfield, Ohio 44403-0464

[21] Appl. No.: 278,811

[22] Filed: Jul. 22, 1994

[51] Int. Cl.⁶ .................................................. A01F 5/44
[52] U.S. Cl. ........................ 604/353; 604/349; 604/351
[58] Field of Search .................................... 604/349–353

[56] References Cited

U.S. PATENT DOCUMENTS

| 2,484,356 | 10/1949 | Ribeiro et al. | 604/353 |
| 2,840,079 | 6/1958 | Conway et al. | 604/350 |
| 3,526,227 | 9/1970 | Appelbaum | 604/350 |
| 3,742,953 | 7/1973 | Lee . | |
| 4,387,726 | 6/1983 | Denard | 604/350 |
| 4,850,986 | 7/1989 | Temple | 604/349 |

FOREIGN PATENT DOCUMENTS

| 674158 | 4/1939 | Germany | 604/349 |

*Primary Examiner*—Randall L. Green
*Assistant Examiner*—Mark O. Polutta
*Attorney, Agent, or Firm*—David J. Archer

[57] ABSTRACT

A urinal device is disclosed for the reception therein of a user's penis. The device includes a support worn by the user for supporting the device relative to the user. A collar is secured to the support for the reception therein of the user's penis. The arrangement is such that in use of the device, the user's penis is inserted through the collar. The collar has a first and a second end. A flexible tubular portion is provided for sealing the device relative to the user's penis, the tubular portion having a first and second extremity. The first extremity engages the first end of the collar and the second extremity sealingly cooperates with the user's penis. A collection device sealingly cooperates with the second end of the collar, the arrangement being such that in use of the device, the user's penis is sealingly supported by the tubular portion so that the user's penis is disposed within the collar.

12 Claims, 2 Drawing Sheets

5,520,671

URINAL DEVICE

FIELD OF THE INVENTION

The present invention relates to a urinal device. More particularly, the present invention relates to a device for the reception therein of a user's penis.

BACKGROUND OF THE INVENTION

Many devices have been manufactured for use by a patient suffering from incontinence. Most of the aforementioned devices include a collection bag for collecting the patient's urine and means for connecting the bag to the body of the user.

In the case of male patients, the prior art urinal devices usually include a connector arrangement through which the user's penis is inserted and a flexible collar which is intended to seal against the user's penis in order to inhibit leakage of urine therepast.

However, the aforementioned prior art devices do not consistently provide a waterproof seal. Furthermore, a patient having undergone surgery and suffering from retracting penis is presented with a serious problem with regard to sealing the unit against leakage.

More particularly, external urinal devices of the aforementioned type have been especially recommended for patients suffering from occasional or complete urinary incontinence. However, such devices have not always been satisfactory in operation.

On the other hand, the device according to the present invention offers comfortable freedom of movement for the user without embarrassment that would be occasioned by leakage of the unit.

The device according to the present invention is particularly useful for men suffering from the medical problem known as "retracting penis". The aforementioned prior art units have been inadequate in overcoming the problem of sealing and securing thereof without subsequent leakage.

Additionally, the prior art arrangements suffer from the drawback of causing irritation to the skin, restriction of movement and the like.

The device according to the present invention is easily fitted to a male patient including those suffering from retracting penis.

The device according to the present invention has a distinct advantage over the prior art arrangements which required special clamps and the like in order to provide adequate sealing.

The device according to the present invention includes a collection device which is either directly connected to a collar or alternatively is connected to the collar by means of latex tubing. An adapter connects the tubing to a leg bag or the like depending on the level of the patient's incontinence.

The device according to the present invention includes a latex sheath which may be cleaned with soap and water thereby providing a hygienic unit.

Ideally, the patient would be provided with two units, one being worn by the patient while the other unit is being washed and dried.

Therefore, it is a primary objective of the present invention to provide a urinary device that overcomes the aforementioned inadequacies of the prior art devices and which makes a considerable contribution to the medical art.

Other objects and advantages of the present invention will be readily apparent to those skilled in the art by reference to the detailed description contained hereinafter taken in conjunction with the annexed drawings.

SUMMARY OF THE INVENTION

The present invention relates to a urinal device for the reception therein of a user's penis. The device includes a support worn by the user for supporting the device relative to the user. A collar is secured to the support for the reception therein of the user's penis. The arrangement is such that in use of the device, the user's penis is inserted through the collar. The collar has a first and a second end. A flexible tubular portion is provided for sealing the device relative to the user's penis, the tubular portion having a first and second extremity. The first extremity sealingly engages the first end of the collar and the second extremity sealingly co-operates with the user's penis. A collection device sealingly co-operates with the second end of the collar. The arrangement is such that, in use of the device, the user's penis is sealingly supported by the tubular portion so that the user's penis is disposed within the collar.

In a more specific embodiment of the present invention, the support means includes a waist band having a first and a second end. Fastening means are secured to the band for fastening the ends together.

The support means is preferably fabricated from cloth and the collar means is of plastics material.

In a specific embodiment of the present invention, the collar is of polyvinylchloride and has a length within the range 2 to 6 inches and an outside diameter within the range 2 to 3 inches. The inside diameter is within the range 1.25 to 1.75 inches.

Additionally, the collar means includes a first portion which extends from the first end of the collar means. The first portion defines an annular groove which cooperates with the first extremity of the tubular means for sealing the tubular means relative to the collar means.

The second portion extends from the first portion to the second end of the collar means. The second portion defines an annular depression for sealingly engaging the collection means.

The second portion has a lesser outside diameter than an outside diameter of the first portion. Additionally, the urinal device includes an O-ring which removably cooperates with the annular depression for removably attaching the collection means to the second end of the collar means.

In a preferred embodiment of the present invention, the tubular means is of latex material and is fabricated from a condom which defines the first and the second extremity. The arrangement is such that the first extremity cooperates with and is stretched over the first end of the collar means. The second extremity is cut off to a size which sealingly cooperates with the user's penis thereby preventing leakage therepast in the event that the user thereof has undergone surgery resulting in retracting penis.

Furthermore, the collection means includes a tubular sleeve which is connected to the second end of the collar means. A collection bag is connected to the tubular sleeve such that the tubular sleeve is disposed between the collar means and the bag.

The collection bag is fabricated from a latex material and the tubular sleeve has an open end which is removably stretched over the second end of the collar means.

Many modifications and variations of the present invention will be readily apparent to those skilled in the art by a consideration of the detailed description contained hereinafter taken in conjunction with the annexed drawings. However, such modifications and variations fall within the spirit and scope of the present invention as defined by the appended claims.

BRIEF DESCRIPTION OF THE DRAWINGS

Similar reference characters refer to similar parts throughout the various views of the drawings.

DETAILED DESCRIPTION OF THE DRAWINGS

Figure 1:
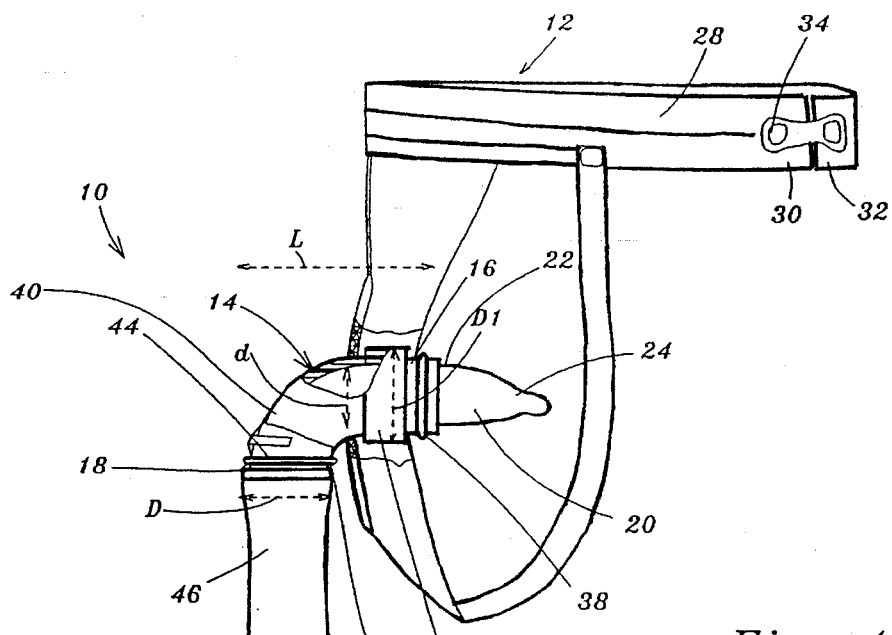
FIG. 1 is a side elevational view partially in sections showing a urinal device according to the present invention.
Figure 3:
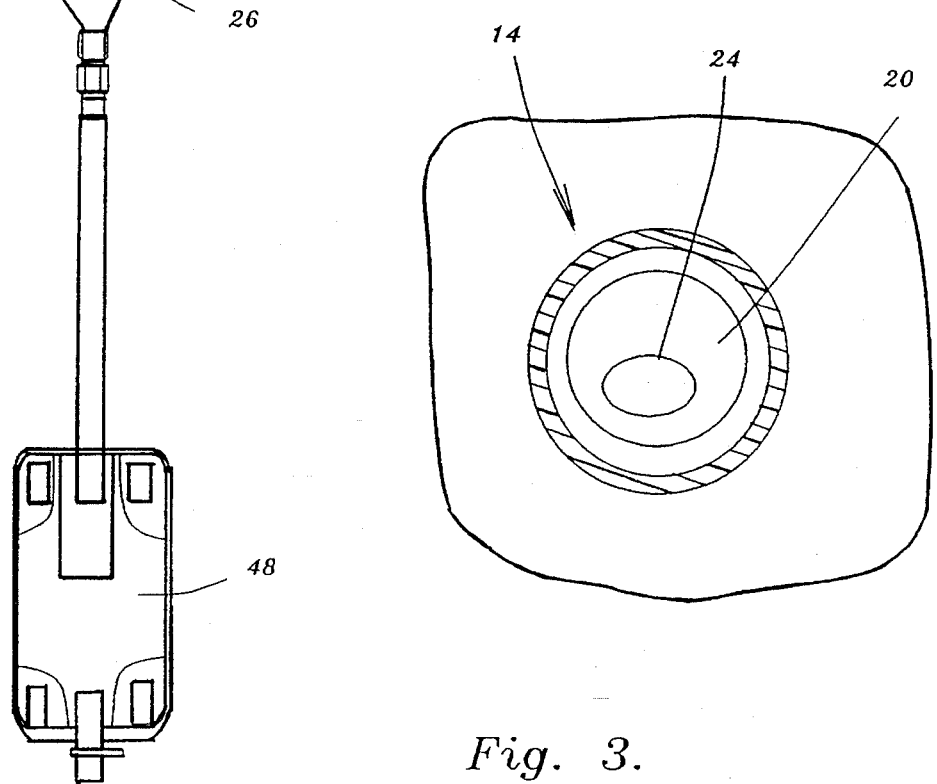
FIG. 3 is a sectional view taken on the line 3—3 of FIG. 2.
Figure 2:
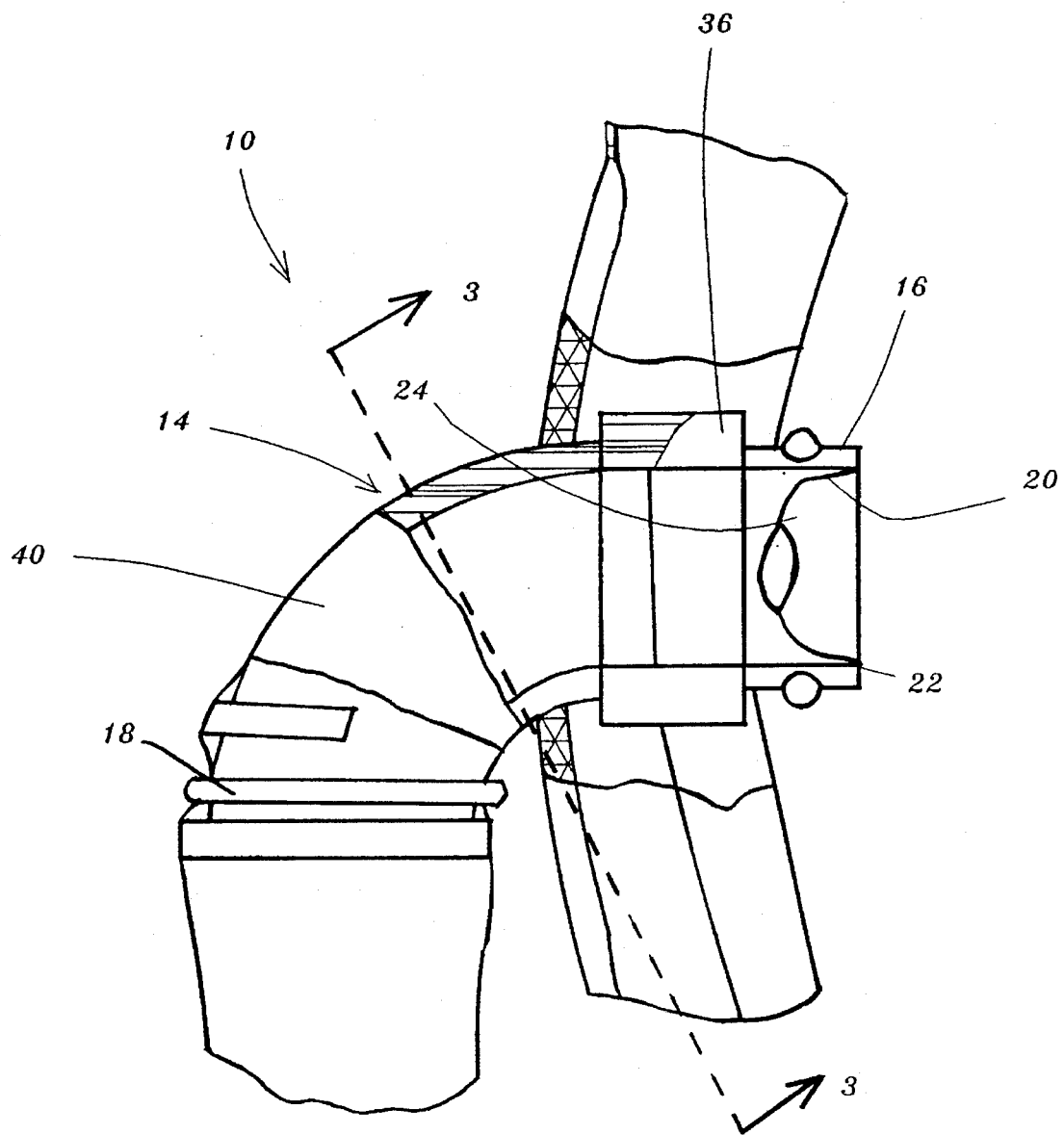
FIG. 2 is an enlarged view partially in section of the collar means of the urinal device shown in FIG. 1.

FIGS. 1-3 show a urinal device generally designated 10 for the reception therein of a user's penis. The device includes support means generally designated 12 worn by the user for supporting the device relative to the user.

A collar means generally designated 14 is secured to the support means 12 for the reception therein of the user's penis, the arrangement being such that in use of the device 10, the user's penis is inserted through the collar means 14, the collar means 14 having a first and a second end 16 and 18 respectively.

In operation of the device 10 according to the present invention, the patient steps into the belted support 12 and pulls the support means 12 up over the user's hips. A flexible tubular means 20 or latex sheath is adjusted over the penis so that it rests securely where the penis joins the stomach.

The penis is adjusted inside the urinal sheath 20 so that the head of the penis protrudes through the front of the narrowest part of the sheath 20. The sheath 20 is trimmed to the correct size of the patient prior to fitting. Petroleum jelly or other ointment recommended by a physician may be beneficial in order to successfully fit the unit.

The device 10 works by preventing the backflow of urine. More particularly, the flexible tubular means 20 having been cut to the correct size seals against the walls of the penis to provide a seal therewith in order to prevent backflow of urine.

The support means 12 is made from a combination of fabrics to ensure breathability while the tubular means 20 is of latex.

More specifically, the flexible tubular means 20 for sealing the device 10 relative to the user's penis includes a first and second extremity 22 and 24 respectively. The first extremity 22 sealingly engages the first end 16 of the collar means 14. The second extremity 24 is cut to size as shown in FIG. 2 so that the second extremity 24 sealingly cooperates with the user's penis.

The device 10 also includes a collection means generally designated 26 which sealingly cooperates with the second end 18 of the collar means 14. The arrangement is such that in use of the device 10, the user's penis is sealingly supported by the tubular means 20 so that the user's penis is disposed within the collar means 14.

The support means 12 also includes a waist band 28 having a first and second end 30 and 32 and fastening means 34 secured to the waist band 28 for fastening the ends 30 and 32 together.

In a preferred embodiment of the present invention the support means 12 is fabricated from cloth.

The collar means 14 is of plastics material and is preferably made from PVC (polyvinylchloride).

The collar means 14 has a length L within the range 2 to 6 inches and an outside diameter D within the range 2 to 3 inches and an inside diameter d within a range 1.25 to 1.75 inches.

The collar means 14 collar means includes a first portion 36 extending from the first end 16 of the collar means 14. The first portion 36 defines an annular groove 38 which cooperates with the first extremity 22 of the tubular means 20 for sealing the tubular means 20 relative to the collar means 14.

A second portion 40 extends between the first portion 36 and the second end 18 of the collar means 14. The second portion 40 defines an annular depression 42 for sealingly engaging the collection means 26.

The second portion 40 has a lesser outside diameter D than an outside diameter D1 of the first portion 36.

An O-ring 44 removably cooperates with the annular depression 42 for removably attaching the collection means 26 to the second end 18 of the collar means 14.

The tubular means 20 is of latex material and is preferably fabricated from a condom defining the first and second extremities 22 and 24, the arrangement being such that the first extremity 22 cooperates with and is stretched over the first end 16 of the collar means 14. The second extremity 24 is cut off to a size which sealingly cooperates with the user's penis thereby preventing leakage therepast in the event that the user thereof has undergone surgery resulting in retracting penis.

The collection means 26 includes a tubular sleeve 46 connected to the second end 18 of the collar means 14.

A collection bag 48 is connected to the tubular sleeve 46 such that the tubular sleeve 46 is disposed between the collar means 14 and the bag 48.

The collection means 26 is fabricated from latex material.

As shown in FIG. 3, the condom is cut off approximately half an inch from the first end of the collar means 14. Typically, in order to fit the device, the foreskin is held back off the head of the penis by the cut portion of the condom.

Washing the device is accomplished by using a chlorex mixture diluted with water.

The inventor of the present invention prior to making the aforementioned invention underwent surgery which resulted in the condition known as "retracting penis".

The inventor subsequently went to several pharmacies and consulted with numerous doctors, nurses and ENT professionals and home health care facilities. However, none of the aforementioned specialists could provide a device for overcoming the problem of leakage associated with the aforementioned retracting penis condition.

According to the inventor's experience there was nothing available on the market that could prevent leakage and provide freedom from pain and discomfort.

In the case of the inventor, the inventor underwent prostectomy and was subsequently fitted with a "Cunningham clamp device." Such device involved penis strangulation which resulted in pain and irritation and also did not prevent leakage.

The device according to the present invention reliably seals against any leakage thereby affording the user thereof freedom of movement without the fear of embarrassment. The device according to the present invention may be worn without irritation for considerable periods without any discomfort to the user thereof.

What is claimed is:

1. A urinal device for the reception therein of a user's penis, said device comprising:

support means worn by the user for supporting said device relative to the user;

collar means secured to said support means for the reception therein of the user's penis said collar means having a length of at least 2 inches, said collar means having a first and a second portion, said first portion having an outside diameter which is greater than an outside diameter of said second portion, said first and second portions being disposed on opposite sides of said support means with said first portion being disposed nearest to the user and between the user and said support means for supporting therein the user's penis, the arrangement being such that in use of the device, the user's penis is inserted through said collar means, said collar means having a first and second end the arrangement being such that in use of the device, any tendency for the user's penis to retract away from said first portion is inhibited thereby preventing leakage therepast;

flexible tubular means for sealing said device relative to the user's penis, said tubular means having a first and second extremity, said first extremity sealingly engaging said first end of said collar means, said second extremity sealingly cooperating with the user's penis;

collection means sealingly cooperating with said second end of said collar means, the arrangement being such that in use of the device, the user's penis is sealingly supported by said tubular means so that the user's penis is disposed within said collar means;

said collection means including:

a tubular sleeve connected to said second end of said collar means;

a collection bag connected to said tubular sleeve such that said tubular sleeve is disposed between said collar means and said bag; and said tubular sleeve being fabricated from latex material.

2. A urinal device as set forth in claim 1 wherein said support means includes:

a waist band having a first and second end;

fastening means secured to said waist band for fastening said ends together.

3. A urinal device as set forth in claim 1 wherein said support means is fabricated from cloth.

4. A urinal device as set forth in claim 1 wherein said collar means is of plastics material.

5. A urinal device as set forth in claim 4 wherein said collar means is of polyvinylchloride.

6. A urinal device as set forth in claim 4 wherein said collar means has a length within the range 2 to 6 inches and an outside diameter within the range 2 to 3 inches and an inside diameter within the range 1.25 to 1.75 inches.

7. A urinal device as set forth in claim 4 wherein said first portion extends from said first end of said collar means, said first portion defining an annular groove which cooperates with said first extremity of said tubular means for sealing said tubular means relative to said collar means;

said second portion extending between said first portion and said second end of said collar means, said second portion defining an annular depression for sealingly engaging said collection means.

8. A urinal device as set forth in claim 7 further including:

an O-ring removably cooperating with said annular depression for removably attaching said collection means to said second end of said collar means.

9. A urinal device as set forth in claim 1 wherein said tubular means is of latex material.

10. A urinal device as set forth in claim 1 wherein said tubular means is fabricated from a condom defining said first and second extremity, the arrangement being such that said first extremity cooperates with and is stretched over said first end of said collar means, said second extremity being cut off to a size which sealingly cooperates with the user's penis thereby preventing leakage therepast in the event that the user thereof has undergone surgery resulting in retracting penis.

11. A urinal device for the reception therein of a user's penis, said device comprising:

support means worn by the user for supporting said device relative to the user;

collar means secured to said support means for the reception therein of the user's penis, said collar means having a length of at least 2 inches, said collar means having a first and a second portion, said first portion having an outside diameter which is greater than an outside diameter of said second portion, said first and second portions being disposed on opposite sides of said support means with said first portion being disposed nearest to the user and between the user and said support means for supporting therein the user's penis, the arrangement being such that in use of the device, the user's penis is inserted through said collar means, said collar means having a first and second end the arrangement being such that in use of the device, any tendency for the user's penis to retract away from said first portion is inhibited thereby preventing leakage therepast;

flexible tubular means for sealing said device relative to the user's penis, said tubular means having a first and second extremity, said first extremity sealingly engaging said first end of said collar means, said second extremity sealingly cooperating with the user's penis;

said tubular means being fabricated from a condom defining said first and second extremity, the arrangement being such that said first extremity cooperates with and is stretched over said first end of said collar means, said second extremity being cut off to a size which sealingly cooperates with the user's penis thereby preventing leakage therepast; and collection means sealingly cooperating with said second end of said collar means, the arrangement being such that in use of the device, the user's penis is sealingly supported by said tubular means so that the user's penis is disposed within said collar means;

said collection means including:

a tubular sleeve connected to said second end of said collar means;

a collection bag connected to said tubular sleeve such that said tubular sleeve is disposed between said collar means and said bag; and said tubular sleeve being fabricated from latex material.

12. A urinal device for the reception therein of a user's penis, said device comprising:

support means worn by the user for supporting said device relative to the user;

collar means secured to said support means for the reception therein of the user's penis, said collar means having a length of at least 2 inches, said collar means having a first and a second portion, said first portion having an outside diameter which is greater than an outside diameter of said second portion, said first and second portions being disposed on opposite sides of said support means with said first portion being disposed nearest to the user and between the user and said support means for supporting therein the user's penis the arrangement being such that in use of the device, the user's penis is inserted through said collar means, said collar means having a first and second end the arrangement being such that in use of the device, any tendency for the user's penis to retract away from said first portion is inhibited thereby preventing leakage therepast;

flexible tubular means fabricated from latex material for sealing said device relative to the user's penis, said tubular means having a first and second extremity, said first extremity sealingly engaging said first end of said collar means, said second extremity sealingly cooperating with the user's penis;

said tubular means being fabricated from a condom which defines said first and second extremity, the arrangement being such that said first extremity cooperates with and is stretched over said first end of said collar means, said second extremity being cut off to a size which sealingly cooperates with the user's penis thereby preventing leakage therepast; and collection means sealingly cooperating with said second end of said collar means, the arrangement being such that in use of the device, the user's penis is sealingly supported by said tubular means so that the user's penis is disposed within said collar means;

said collection means including:

a tubular sleeve connected to said second end of said collar means;

a collection bag connected to said tubular sleeve such that said tubular sleeve is disposed between said collar means and said bag; and said tubular sleeve being fabricated from latex material.

\* \* \* \* \*

UNITED STATES PATENT AND TRADEMARK OFFICE
CERTIFICATE OF CORRECTION

PATENT NO. : 5,520,671
DATED : May 28, 1996
INVENTOR(S) : Richard E. Bouser

It is certified that error appears in the above-indentified patent and that said Letters Patent is hereby corrected as shown below:

Column 2, line 39 delete "scaling" and insert therefor --sealing--

Signed and Sealed this

Tenth Day of September, 1996

Attest:

BRUCE LEHMAN

*Attesting Officer*          Commissioner of Patents and Trademarks